United States Patent
Mori et al.

(10) Patent No.: US 8,088,264 B2
(45) Date of Patent: Jan. 3, 2012

(54) GAS SENSOR ELEMENT AND GAS SENSOR

(75) Inventors: Kentaro Mori, Inuyama (JP); Nobuo Furuta, Kasugai (JP); Shigeki Mori, Seki (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 378 days.

(21) Appl. No.: 12/349,764

(22) Filed: Jan. 7, 2009

(65) Prior Publication Data

US 2009/0173630 A1 Jul. 9, 2009

(30) Foreign Application Priority Data

Jan. 8, 2008 (JP) ................................ P2008-000957

(51) Int. Cl.
*G01N 27/26* (2006.01)
*G01N 27/407* (2006.01)
(52) U.S. Cl. ....................................... 204/426; 204/427
(58) Field of Classification Search .................. 204/426, 204/427, 429
See application file for complete search history.

(56) References Cited

U.S. PATENT DOCUMENTS

| 5,443,711 | A | | 8/1995 | Kojima et al. |
| 5,472,591 | A | * | 12/1995 | Saito et al. ..................... 204/429 |
| 6,660,145 | B2 | * | 12/2003 | Hotta et al. .................... 204/429 |

FOREIGN PATENT DOCUMENTS

JP 1-203963 8/1989

* cited by examiner

*Primary Examiner* — Bruce Bell
(74) *Attorney, Agent, or Firm* — Stites & Harbison PLLC; Jeffrey A. Haeberlin; Nicolo Davidson

(57) ABSTRACT

A gas sensor element for detecting a specific gas component contained in a gas to be measured includes: a solid electrolyte layer; a first electrode disposed on the solid electrolyte layer; a second electrode disposed on the solid electrolyte layer; and a porous layer disposed on one of the first electrode and the second electrode such that the gas to be measured is introduced from the outside of said gas sensor element and passes through the porous layer to at least one of the first electrode and the second electrode. The porous layer includes: a first porous layer including a first ceramic porous body which does not include noble metal particles dispersed therein; and a second porous layer provided on the first porous layer and including a second ceramic porous body and noble metal particles dispersed therein.

7 Claims, 8 Drawing Sheets

GAS SENSOR ELEMENT AND GAS SENSOR

CROSS-REFERENCE TO RELATED APPLICATIONS

This application is based on and claims priority to Japanese Patent Application No. 2008-000957 filed Jan. 8, 2008, the above application incorporated herein by reference in its entirety.

BACKGROUND OF THE INVENTION

1. Field of the Invention

The present invention relates to a gas sensor element and a gas sensor used for measuring a gas, such as combustion gas or exhaust gas, for example, of a combustor or an internal combustion engine.

2. Description of Related Art

An oxygen sensor or an air-fuel ratio sensor for detecting the concentration of oxygen contained in exhaust gas, or for improving combustion efficiency or controlling the combustion of an internal combustion engine of a motor vehicle, is known.

A technique applied for the oxygen sensor in which a catalyst layer covers a detecting electrode of a gas to be measured is known. This technique is disclosed, for example, in Japanese patent publications JP-A-1-203963, JP-A-2-151755 and JP-A-2002-181769. The catalyst layer includes a porous layer of alumina or titania or the like and noble metal particles supported by the porous layer. Consequently, unburnt gas ($H_2$, NOx, HC, etc.) in the gas to be measured is burnt before the unburnt gas reaches the detecting electrode, which prevents an influence on a measurement, improves a detection accuracy and decreases a deviation of a λ point (λ: air excess ratio).

This catalyst layer is formed by a following method: first, alumina or titania is injected or applied to a solid electrolyte member on which the detecting electrode is formed to form the porous layer; and next, this porous layer is dipped in noble metal salt solution including the noble metal particles or ions, and then dried and sintered to form the catalyst layer in which the noble metal particles are supported by the porous layer. In the catalyst layer thus formed, the noble metal particles are uniformly dispersed and supported by the porous layer.

BRIEF SUMMARY OF THE INVENTION

In the above-described technique, in order to enhance the combustion of the unburnt gas in the catalyst layer, it is seemingly preferable to increase an amount of the noble metal particles supported by the catalyst layer. However, even when the amount of the noble metal particles supported by the catalyst layer is increased, the degree of combustion of the unburnt gas is not improved much, and a response speed of the gas sensor is rather deteriorated. This phenomenon is considered to occur because the noble metal particles adsorb or desorb oxygen as well as the unburnt gas. The adsorption or desorption of the oxygen by the noble metal particles is also increased as the amount of the noble metal particles supported by the catalyst layer is increased, which also deteriorates the response speed to the change of the gas to be measured.

The present invention was made in consideration of the above circumstances, and an object thereof is to provide a gas sensor element and a gas sensor capable of effectively burning unburnt gas in gas to be measured and suppressing the deterioration of the response speed of the sensor, without providing noble metal particles uniformly dispersed in and support by a catalyst layer.

In a first aspect, a gas sensor element for detecting a specific gas component contained in a gas to be measured, said gas sensor element includes: a solid electrolyte layer; a first electrode disposed on the solid electrolyte layer; a second electrode disposed on the solid electrolyte layer and paired with the first electrode; and a porous layer disposed on one of the first electrode and the second electrode such that the gas to be measured is introduced from outside of the gas sensor element and passes through the porous layer to at least one of the first electrode and the second electrode, wherein the porous layer comprises: a first porous layer comprising a first ceramic porous body which does not include noble metal particles dispersed therein; and a second porous layer provided on the first porous layer and comprising a second ceramic porous body and noble metal particles dispersed therein.

An exemplified porous layer comprising a first porous layer and a second porous layer is a particle dispersed layer including an internal region and a surface region provided on the internal region. In this case, the internal region serves as an example of the first porous layer, and the surface region serves as an example of the second porous layer. As described above, since the noble metal particles are not uniformly dispersed in the porous layer and are provided only in the surface region of the particle dispersed layer, the gas to be measured is largely uninfluenced by the adsorption or desorption of oxygen by the noble metal particles and is introduced to an internal portion of the particle dispersed layer, so that the deterioration of the response speed of such a gas sensor can be suppressed. Furthermore, since the noble metal particles are provided in the particle dispersed layer, unburnt gas in the gas to be measured can be effectively burnt.

Further, since the noble metal particles are dispersed and provided only in the surface region of the particle dispersed layer, the gas to be measured introduced to the surface region of the particle dispersed layer from the outside is largely uninfluenced by the adsorption or desorption of the oxygen by the noble metal particles, even in the surface region, and is introduced to the internal region of the particle dispersed layer. Thus, the deterioration of the response speed of the gas sensor can be suppressed.

In this specification, the "surface region of the particle dispersed layer" indicates a region where an exposed outermost surface is formed when only the particle dispersed layer is visually viewed. Specifically, by considering that the outermost surface of the particle dispersed layer has irregularities (protruding portions and recessed portions), the surface region indicates a region in a direction of a thickness of the layer where the irregularities (protruding and recessed portions) are formed.

Further, the "porous layer" may be interposed between the outside of the gas sensor element and the one of the first and second electrodes so that the gas to be measured passes from outside of the gas sensor element to at least one of the first electrode and the second electrode. Therefore, the porous layer may directly or indirectly cover the electrode exposed to the gas to be measured or may be disposed to close a gas introducing passage arranged to expose the electrode to be exposed to the gas to be measured. Further, the porous layer may include a single layer or a plurality of layers.

Further, the "noble metal particles are dispersed and arranged" indicates that the noble metal particles are dispersed and arranged so that a material forming the particle dispersed layer is exposed when only the particle dispersed layer is visible. The noble metal particles may be arranged by single particles or a plurality of coupled particles.

In one implementation, the noble metal particles comprise one or more elements selected from a group consisting of Pt, Pd, Rh and Ru. Accordingly, the unburnt gas in the gas to be measured can be efficiently burnt.

In another implementation, the noble metal particles are dispersed and arranged only in the second porous layer by a sputtering method, a PVD method or a printing method. Accordingly, the noble metal particles can be easily dispersed only in the second layer, for example, the surface region of the particle dispersed layer.

The porous layer may further comprise a non-particle dispersed layer that does not contain the noble metal particles. In addition to the first and second porous layers, for example, the gas sensor element may possibly require a porous layer such as a water-proof layer for preventing water from directly splashing on the gas sensor element when the gas sensor element is covered with water, a diffusion rate controlling layer for controlling the introduced gas to be measured when the gas to be measured is introduced to the inside of the gas sensor element, or a protecting layer for protecting the electrode. In this case, the particle dispersed layer containing the noble metal particles and the non-particle dispersed layer for another purpose are separately provided as described above, so that the particle dispersed layer and the non-particle dispersed layer can sufficiently fulfill their functions.

The non-particle dispersed layer may be disposed closer to the one electrode than the first and second porous layers. Accordingly, after the second porous layer (e.g., the particle dispersed layer) burns the unburnt gas, the non-particle dispersed layer can fulfill its function. Therefore, the respective functions of the particle dispersed layer and the non-particle dispersed layer can be fulfilled.

In yet another implementation, the porous layer further comprises: a third porous layer provided on the second porous layer, the third porous layer comprising a third ceramic porous body which does not include noble metal particles dispersed therein; and a fourth porous layer provided on the third porous layer and comprising a fourth ceramic porous body and noble metal particles dispersed therein. Accordingly, since the second and fourth porous layers (e.g., the surface regions of the particle dispersed layers) containing the noble metal particles are separately provided, the thickness of the surface regions can be respectively decreased and the deterioration of responsiveness can be prevented. Further, a total amount of the noble metal particles supported by the particle dispersed layers can be increased, so that the exhaustion of the noble metal particles due to a use for a long period can be suppressed and durability can be improved.

An amount of the noble metal particles in the fourth porous layer may be larger than an amount of the noble metal particles in the second porous layer. Accordingly, the unburnt gas in the gas to be measured can be effectively burnt.

In accordance with another aspect, a gas sensor includes: the gas sensor element as described above, the gas sensor element having a plate-like shape, comprising a leading end side portion and a base end, and defining an axial direction, the leading end side portion of the gas sensor element being exposed to a gas to be measured; and a metal shell supporting the gas sensor element such that the leading end side portion protrudes from the metal shell. Accordingly, since the noble metal particles are dispersed and arranged only in the second porous layer of the first and second porous layers, the gas sensor element and the gas sensor are capable of burning unburnt gas in the gas to be measured and suppressing the deterioration of the response speed of the sensor.

Other features and advantages of the invention will be set forth in, or apparent from, the detailed description of the exemplary embodiments of the invention found below.

DETAILED DESCRIPTION OF EXEMPLARY EMBODIMENTS OF THE INVENTION

Now, an embodiment of the present invention will be described below.

Figure 1:
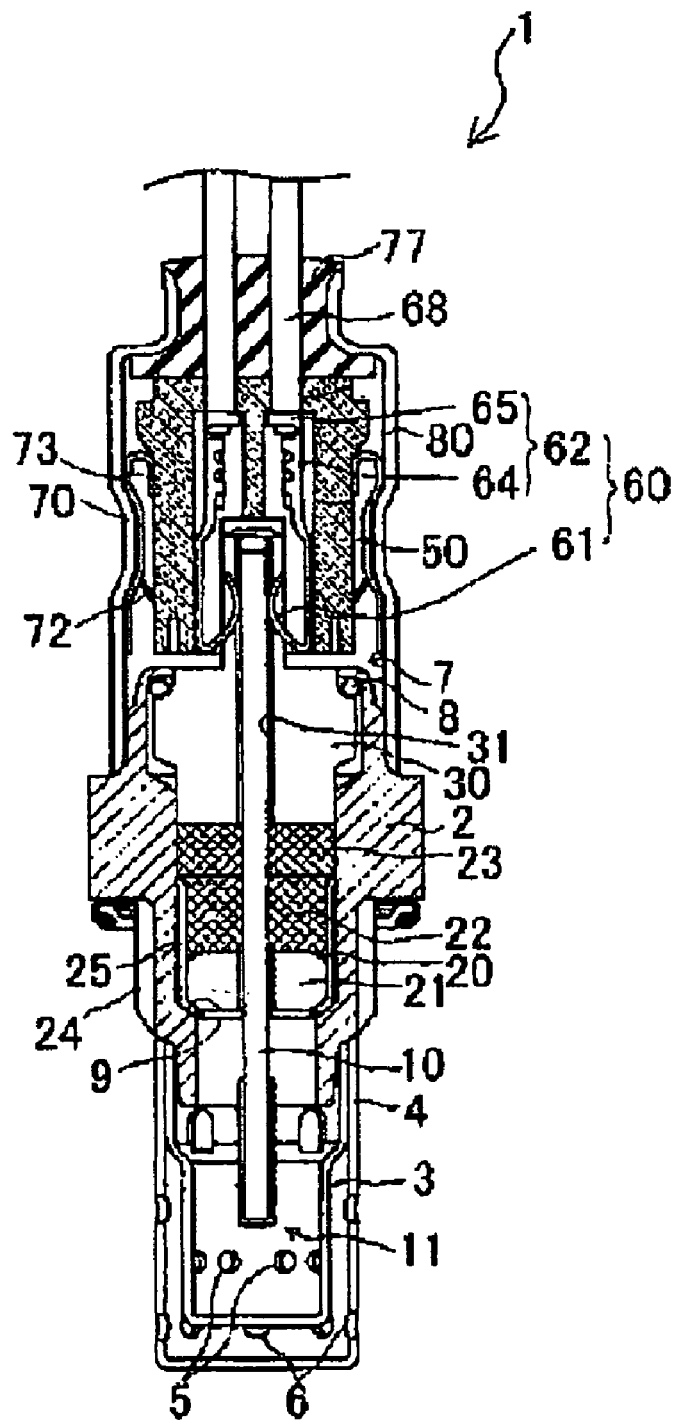
FIG. 1 is a sectional view taken along a longitudinal direction of a gas sensor (e.g., an oxygen sensor) according to a first exemplary embodiment of a gas sensor of the present invention.

FIG. 1 shows a sectional view along a longitudinal direction of a gas sensor 1 (e.g., an oxygen sensor) according to a first exemplary embodiment of the present invention. A lower side of FIG. 1 is referred to as a "leading end" side and an upper side is referred to as a "base end" side.

The gas sensor 1 is an assembly to which a gas sensor element 10 for detecting the concentration of oxygen is attached. The gas sensor 1 includes: a gas sensor element 10 having a plate-like shape and extending in an axial direction; a cylindrical metal shell 2 having a screw portion 24 formed on an external surface, for being fixed to an exhaust pipe; a cylindrical ceramic sleeve 30 having an insert hole 31 of the gas sensor element 10 and arranged inside the metal shell 2; a cylindrical separator 50 made of alumina and having an insert hole for a terminal fitting 60 connected to electrode terminals 120a, 120b, 140a, 140b provided in the base end portion of the gas sensor element 10; a cylindrical grommet 77 provided on the base end side of the separator 50, made of fluoride rubber and having insert holes for four lead wires 68 (only two lead wires are shown) connected to the terminal fitting 60; and a cylindrical external cylinder 80 made of stainless steel, externally holding the separator 50 and the grommet 77 and connected to the base end of the metal shell 2.

The metal shell 2 defines a through hole 25 in the axial direction and has a shelf portion 9 protruding radially inwardly in through hole 25. This shelf portion 9 includes an inwardly tapered surface that is inclined relative to a plane perpendicular to the axial direction. Further, the metal shell 2 holds the gas sensor element 10 in a state in which a leading end side of the gas sensor element 10 is arranged outside a leading end side of the metal shell 2.

In the through hole 25 of the metal shell 2, an annular ceramic holder 21 for enclosing a radial periphery of the gas sensor element 10, powder filled layers (talc ring) 22, 23, and the ceramic sleeve 30 are laminated in order from the leading end side to the base end side. Further, between the ceramic sleeve 30 and the base end portion of the metal shell 2, a crimping packing 8 is arranged. Between the ceramic holder 21 and the shelf portion 9 of the metal shell 2, a metal holder 20 is provided for holding the talc rings 22, 23, and the ceramic holder 21, and maintaining an air-tightness. The base end portion of the metal shell 2 is crimped so as to press the ceramic sleeve 30 toward the leading end side through the crimping packing 8 to form a crimping portion 7.

The talc rings 22, 23 are compressed by a crimping operation so that the gas sensor element 10 is fixed at a prescribed position in the metal shell 2.

As shown in FIG. 1, an external protector 4 and an internal protector 3 are welded to an external peripheral surface of the leading end side of the metal shell 2. The protectors 3, 4 are made of metal (for example, stainless steel or the like) and cover a protruding portion (a detecting portion) 11 of the gas sensor element 10. A plurality of hole portions 5, 6 are formed in the protectors 3, 4, respectively.

The external cylinder 80 is fixed to the external peripheral surface of the base end side of the metal shell 2. The external cylinder 80 externally holds the separator 50 and the grommet 77 and the base end portion of the external cylinder 80 is crimped to secure the separator 50 and the grommet 77.

Further, a substantially cylindrical holding fitting 70 made of metal is interposed between the separator 50 and the external cylinder 80. A protruding portion 72 that protrudes inwardly is formed, in an intermediate portion of an internal peripheral surface of the holding fitting 70. The base end of the holding fitting 70 is folded back inward to form a folded portion 73. The protruding portion 72 and the folded portion 73 are brought into resilient contact with the external peripheral surface of the separator 50. Therefore, even when an impact is applied to the gas sensor 1, the impact is not directly transmitted to the separator 50.

The terminal fitting 60 includes a base portion 62 for crimping and connecting the lead wires 68 and a leading end portion 61 extending from the base portion 62 and folded back inwardly. The base portion 62 further includes a first crimping portion 65 for crimping external peripheries of insulating coats of the lead wires 68 and a second crimping portion 64 for crimping and electrically connecting conductors formed by peeling and exposing the ends of the lead wires 68. The leading end portion 61 includes a plurality of inwardly folded back portions arranged so as to be respectively opposed to the electrode terminals 120a, 120b, 140a, 140b formed on the front and back sides of the base end of the gas sensor element 10. When the electrode terminals are interposed between the opposed and inwardly folded back portions, the leading end portion 61 is urged to the electrode terminals 120a, 120b, 140a, 140b by a resilient force of the leading end portion 61 and electrically connected to the electrode terminals 120a, 120b, 140a, 140b.

Now, the configuration of the gas sensor element 10 will be described by referring to a development view (i.e., an exploded view) shown in FIG. 2. The gas sensor element 10 has an elongated plate-like shape. The gas sensor element 10 includes an oxygen concentration cell 12 configured to detect the concentration of oxygen in exhaust gas, and a heater portion 14 laminated to the oxygen concentration cell 12.

Figure 2:
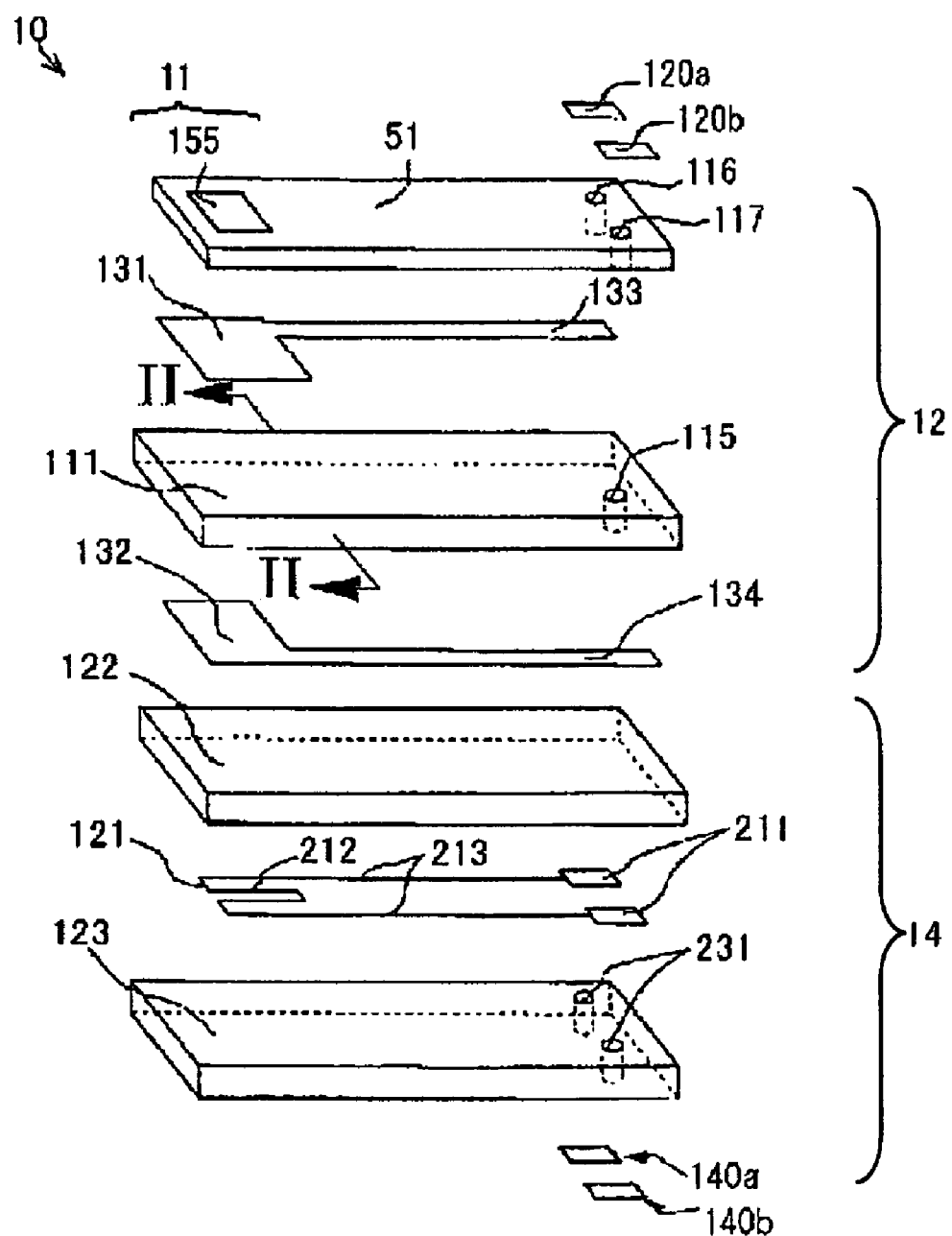
FIG. 2 is an exploded view of a gas sensor element of the gas sensor of FIG. 1.

The oxygen concentration cell 12 includes a solid electrolyte layer 111, a rectangular detecting electrode (an example of a first electrode) 131 provided on a left side, as shown in FIG. 2, of an upper surface of the solid electrolyte layer 111 and a reference electrode (an example of a second electrode paired with the first electrode) 132 opposing the detecting electrode 131 through the solid electrolyte layer 111. Further, a detecting lead portion 133 is extended toward a right side, as shown in FIG. 2, in the longitudinal direction from the detecting electrode 131. Similarly, a reference lead portion 134 is extended toward a right side, as shown in FIG. 2, in the longitudinal direction from the reference electrode 132.

The surface of the detecting electrode 131 is covered with a porous protecting layer 155 for protecting the detecting electrode 131. Further, an insulating layer 51 is formed that encloses the porous protecting layer 155 and protects the lead portion 133 on the solid electrolyte layer 111. A laminated body located in the leading end of the gas sensor element 10 and including the detecting electrode 131 and the reference electrode 132 is referred to as a detecting portion 11.

Further, an end portion of the reference lead portion 134 is electrically connected to the electrode terminal 120b disposed at the right end portion, as shown in FIG. 2, of the upper surface of the insulating layer 51 via a through hole 115 formed in the solid electrolyte layer 111 and a through hole 117 formed in the insulating layer 51. Further, an end portion of the detecting lead portion 133 is electrically connected to the electrode terminal 120a disposed at the right end portion, as shown in FIG. 2, of the upper surface of the insulating layer 51 via a through hole 116 formed in the insulating layer 51.

The heater portion 14 includes two insulating layers 122 and 123 and a heat generating resistor 121 extending in the longitudinal direction and interposed between the two insulating layers 122 and 123. The heat generating resistor 121 includes: a heat generating portion 212 including a heat generating wire having a serpentine or meandering shape and located just below the detecting electrode 131; a pair of lead portions 213 extending longitudinally from the end portion of the heat generating portion 212; and end portions 211 connected to the end portions of the lead portions 213. The end portions 211 are electrically connected to the electrode terminals 140a, 140b disposed at the right end, as shown in FIG. 2, of a lower surface of the insulating layer 123 via two through holes 231 formed in the insulating layer 123, respectively.

The solid electrolyte layer 111 can include, for example, a partially-stabilized zirconia (obtained by adding yttria or calcia as a stabilizer to zirconia). The insulating layers 122, 123 may include alumina as a main or primary component. The detecting electrode 131, the reference electrode 132, the heat generating portion 212, the lead portions 133, 134, 213, the end portions 211 and the electrode terminals 120a, 120b, 140a, 140b may contain, for example, Pt, Rh, Pd or the like.

The porous protecting layer 155 may contain a material including, for example, alumina as a main or primary component and a sublimate material such as carbon mixed therewith. The carbon is sintered to be sublimated so that the porous protecting layer 155 is formed. The porous protecting layer 155 in the first embodiment is an example of a non-particle dispersed layer. In other words, the porous protecting layer 155 includes a ceramic porous body which does not include noble metal particles dispersed therein.

Now, one example of an operation of the gas sensor element 10 will be described below. Initially, the oxygen concentration cell 12 is heated up to an activating temperature by the heater portion 14. Then, a minute current is supplied between the detecting electrode 131 and the reference electrode 132 of the oxygen concentration cell 12 so that an amount of oxygen to become a reference concentration is pumped from the detecting electrode 131 to the reference electrode 132 for use as an oxygen reference. Then, in accordance with the concentration of the oxygen in the gas to be measured (e.g., exhaust gas) that contacts the detecting electrode 131 introduced from the porous protecting layer 155 side, an electromotive force between the detecting electrode 131 and the reference electrode 132 suddenly (i.e., abruptly) changes in the vicinity of a theoretical air fuel ratio ($\lambda=1$), so that it is possible to detect whether the exhaust gas is in a lean state or in a rich state. Here, the term "rich" means an atmosphere in which the ratio of the oxygen is low relative to $\lambda=1$. The term "lean" means an atmosphere in which the ratio of the oxygen is high relative to $\lambda=1$.

In this embodiment, reference gas is stored in the reference electrode 132. Alternatively, a space (an atmospheric air introducing hole) for introducing atmospheric air may be provided between the reference electrode 132 and the insulating layer 122.

Figure 3:
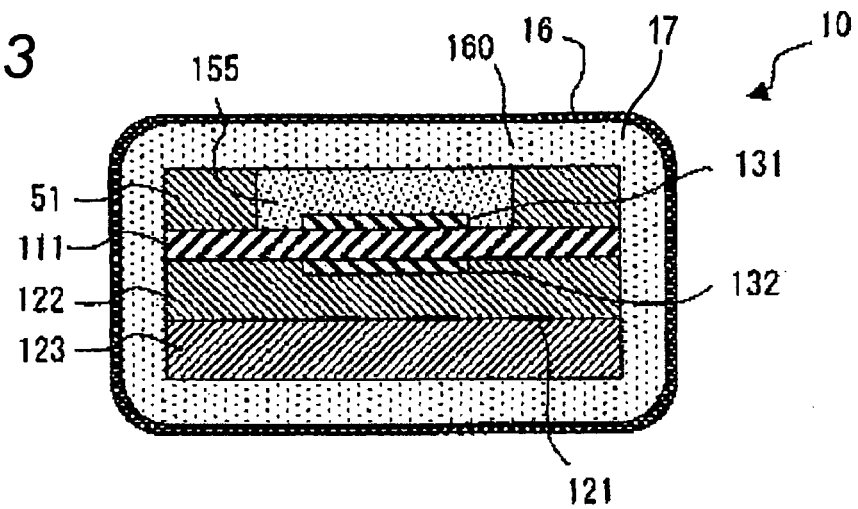
FIG. 3 is a sectional view taken along the line II-II of FIG. 2.

FIG. 3 is a sectional view taken along a line II-II of FIG. 2. In FIG. 3, a particle dispersed layer 160 omitted in FIG. 2 is shown. In this embodiment, the particle dispersed layer 160 covers an entire external peripheral surface of the detecting portion 11 of the gas sensor element 10. The particle dispersed layer 160 can prevent cracking generated in an element main body even when water drops adhered to the element main body. The particle dispersed layer 160 may include, for example, $MgO-Al_2O_3$ spinel and titania as main or primary components. In other words, the particle dispersed layer includes a ceramic porous body.

The particle dispersed layer 160 includes an internal region 17 and a surface region 16 provided on the internal region 17. In the surface region 16 of the particle dispersed layer 160, noble metal particles are provided in a dispersed state. This surface region 16 is formed over the entire portion of the surface of the particle dispersed layer 160. The noble metal particles have a catalyst function for burning unburnt gas ($H_2$, $NO_x$, HC, etc.) in the gas to be measured before the unburnt gas reaches the detecting electrode to improve a detection accuracy of the gas sensor 1 and reduce a deviation of what is called a $\lambda$ point.

In the present embodiment, the noble metal particles are dispersed and arranged only in the surface region 16 of the particle dispersed layer 160 so that the noble metal particles are not contained in the internal region 17 of the particle dispersed layer 160. In other words, the particle dispersed layer 160 includes: the internal region 17 serving as an example of a first porous layer including a first ceramic porous body which does not include noble metal particles dispersed therein; and the surface region 16 serving as an example of a second porous layer provided on the first porous layer and including a second ceramic porous body and noble metal particles dispersed therein. Since the noble metal particles are not uniformly dispersed in the particle dispersed layer 160 but are arranged only in the surface region 16 of the particle dispersed layer 160, the gas to be measured is largely uninfluenced by the adsorption or desorption of oxygen by the noble metal particles and is introduced to the internal region 17 of the particle dispersed layer 160. Thus, the deterioration of the response speed of the gas sensor 1 is suppressed. Furthermore, since the noble metal particles are arranged in the particle dispersed layer 160, the unburnt gas in the gas to be measured can be effectively burnt.

Further, since the noble metal particles are dispersed and arranged only in the surface region 16 of the particle dispersed layer 160, the gas to be measured introduced to the surface region 16 of the particle dispersed layer 160 from an outside of the gas sensor 1 is largely uninfluenced by the adsorption or desorption of the oxygen by the noble metal particles even in the surface region 16 and can be easily introduced to the internal region 17 of the particle dispersed layer 160, so that the deterioration of the response speed of the gas sensor 1 is suppressed.

As the noble metal particles, one or more kinds of elements selected from a group consisting of Pt, Pd, Rh and Ru can be used. Two or more kinds of the single noble metals may be provided in the porous layer. Further, an alloy of these noble metals may be used.

As a method for dispersing and arranging the noble metal particles only in the surface region 16 of the particle dispersed layer 160, for example, a sputtering method, a PVD method or a printing method may be exemplified.

In the case of the sputtering method, since the atoms of the noble metal particles used as a target are ejected with a high rectilinear property and collide with the surface of the particle dispersed layer 160, the noble metal particles are stuck only to the surface region 16 of the particle dispersed layer 160.

Also in the case of the PVD (physical vapor deposition) method, since the noble metal particles have directivity, the noble metal particles are adhered only to the surface region 16 of the particle dispersed layer 160.

In the case of the printing method, since a paste obtained by mixing the noble metal particles with a binder is applied to the surface of the particle dispersed layer 160, the noble metal particles are adhered only to the surface region 16 of the particle dispersed layer 160.

The porous protecting layer 155 in which the noble metal particles are not arranged is provided as a protecting layer for protecting the electrode. Accordingly, the porous protecting layer 155 is separated from the particle dispersed layer 160, so that the porous protecting layer 155 and the particle dispersed layer 160 can function sufficiently. Since the porous protecting layer 155 is arranged closer to the detecting electrode 131 than the particle dispersed layer 160, after the unburnt gas in the gas to be measured is more effectively burnt in the particle dispersed layer 160, the porous protecting layer 155 can function sufficiently.

Specifically, the surface region 16 is defined as follows. When a section of the particle dispersed layer 160 is observed visually or by an SEM, an imaginary outermost surface is defined by connecting outermost surfaces of the particle dispersed layer 160. Then, the surface region 16 of the particle dispersed layer 160 is defined as a region sandwiched between an imaginary line connecting protruding portions and an imaginary line connecting recessed portions relative to the imaginary outermost surface.

Figure 4A:
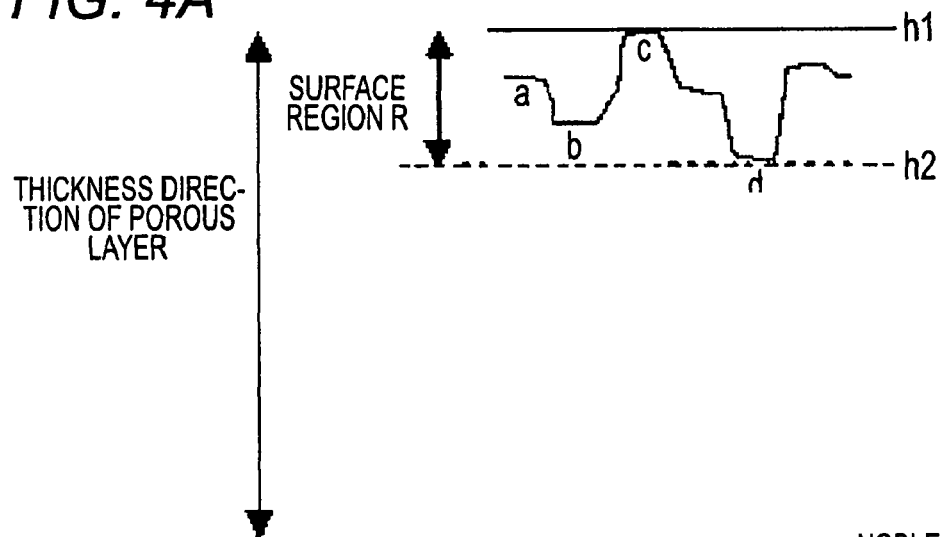
FIG. 4A is a schematic view showing a position of a surface region in a particle dispersed layer.
Figure 4B:
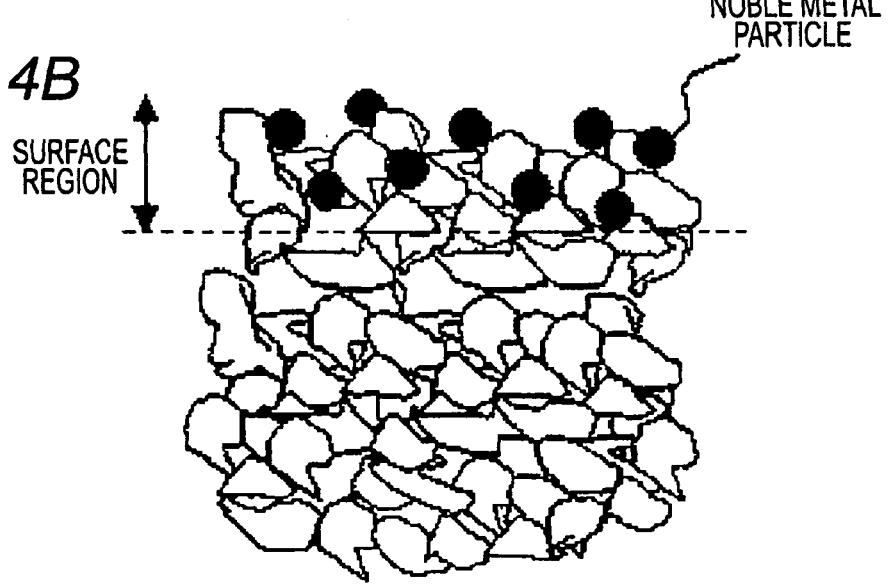
FIG. 4B is a schematic view showing a state that noble metal particles are arranged only in the surface region of the particle dispersed layer and produced by a sputtering method.

FIGS. 4A and 4B show the surface region 16 in the particle dispersed layer 160 (FIG. 4A). The outermost surface of the particle dispersed layer 160 has protruding portions and recessed portions such that the outermost surfaces includes points "a" to "d" having different heights in the direction of the thickness of particle dispersed layer 160 (the "thickness direction"). In this case, an area R in the thickness direction formed by connecting the height h1 at the point "c" as the highest protrusion to the height h2 of the point "d" as the lowest recess indicates the surface region 16. In other words, the surface region 16 is defined as a region between the most protruding point and most recessed point of the particle dispersed layer 160 in the thickness direction.

FIG. 4B shows a schematic arrangement of the noble metal particles dispersed only in the surface region 16 of the particle dispersed layer 160 by the sputtering method. As shown in FIG. 4B, the noble metal particles ejected vertical to the particle dispersed layer 160 by the sputtering method collide with meshes on the surface or on a slightly internal portion from the surface (in this case, on the imaginary outermost surface of the particle dispersed layer 160) of a mesh structure of the particle dispersed layer 160 and adhered to the particle dispersed layer 160. Accordingly, the noble metal particles do not enter the internal region 17 of the particle dispersed layer 160. That is, the noble metal particles stick to the outermost surface (including the irregularities) that is seen, for example, when only the particle dispersed layer 160 is visually observed or viewed.

Figure 5:
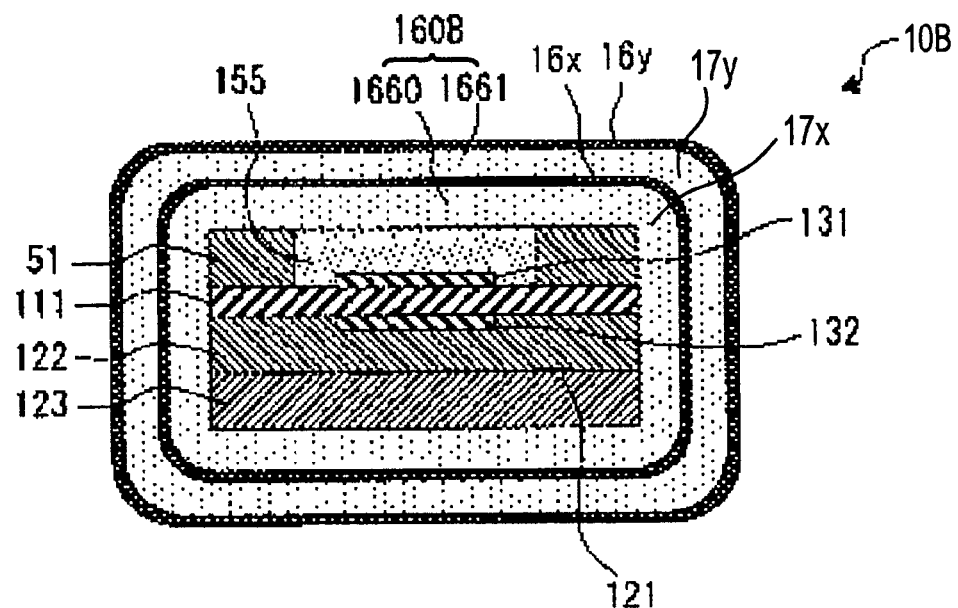
FIG. 5 is a sectional view of a gas sensor element (e.g., an oxygen sensor) according to a second embodiment of the present invention.

FIG. 5 shows a sectional view (taken in the same direction as that of FIG. 3) of a gas sensor element 10B of a gas sensor (an oxygen sensor) according to a second embodiment of the present invention. Since the gas sensor according to the second embodiment is the same as the gas sensor according to the first embodiment except that the structure of a particle dispersed layer 160B is different from that of the particle dispersed layer 160 of the first embodiment, an explanation of the same portions will be omitted.

In the gas sensor according to the second embodiment, the particle dispersed layer 160B includes a first particle dispersed layer 1660 and a second particle dispersed layer 1661 laminated in this order. The first particle dispersed layer 1660 includes an internal region 17x and a surface region 16x provided on the internal region 17x. Noble metal particles are dispersed and arranged only in the surface region 16x of the first particle dispersed layer 1660. In other words, the first particle dispersed layer 1660 includes: the internal region 17x serving as an example of a first porous layer including a first ceramic porous body which does not include noble metal particles dispersed therein; and the surface region 16x serving as an example of a second porous layer provided on the first porous layer and including a second ceramic porous body and noble metal particles dispersed therein. Further, the second particle dispersed layer 1661 includes an internal region 17y provided on the surface region 16x of the first particle dispersed layer 1660 and a surface region 16y provided on the internal region 17y. Noble metal particles are dispersed and arranged only in a surface region 16y of the second particle dispersed layer 1661. In other words, the second particle dispersed layer 1662 includes: the internal region 17y serving as an example of a third porous layer provided on the second porous layer, the third porous layer including a third ceramic porous body which does not include noble metal particles dispersed therein; and the surface region 16y serving as an example of a fourth porous layer provided on the third porous layer and including a fourth ceramic porous body and noble metal particles dispersed therein. Kinds of elements of the noble metal particles arranged in the surface regions 16x and 16y in the second embodiment are the same as those of the first embodiment.

The particle dispersed layer 160B can be produced as described below. Initially, the first particle displayed layer 1660 is formed on the gas sensor element 10B by a spray injection and then thermally treated, and thereafter the noble metal particles are dispersed and arranged in the surface region 16x of the first particle dispersed layer 1660 by sputtering. Then, the second particle dispersed layer 1661 is formed on the surface region 16x by the spray injection and then thermally treated, and thereafter, the noble metal particles are dispersed and arranged in the surface region 16y by sputtering to form the particle dispersed layer 160B.

Accordingly, the particle dispersed layer 160B includes the two layers of the first particle dispersed layer 1660 and the second particle dispersed layer 1661. Thus, since the surface regions 16x and 16y of the particle dispersed layer 160B in which the noble metal particles are arranged can be separately arranged, the thickness of each of the surface regions 16x and 16y can be reduced, and a deterioration of the responsiveness can be prevented more than that of a single-layered particle dispersed layer. Further, a total amount of the noble metal particles supported by the particle dispersed layer can be increased so that exhaustion of the noble metal particles due to a use for a long period can be suppressed, and durability can be improved.

Further, in this embodiment, an amount of the noble metal particles in the surface region 16y of the second particle dispersed layer 1661 is larger than an amount of the noble metal particles arranged in the surface region 16x of the first particle dispersed layer 1660. A method for changing the amount of the noble metal particles arranged in the surface region can be realized by providing a difference in spray injection time. Thus, gas to be measured can be effectively burnt.

Figure 6:
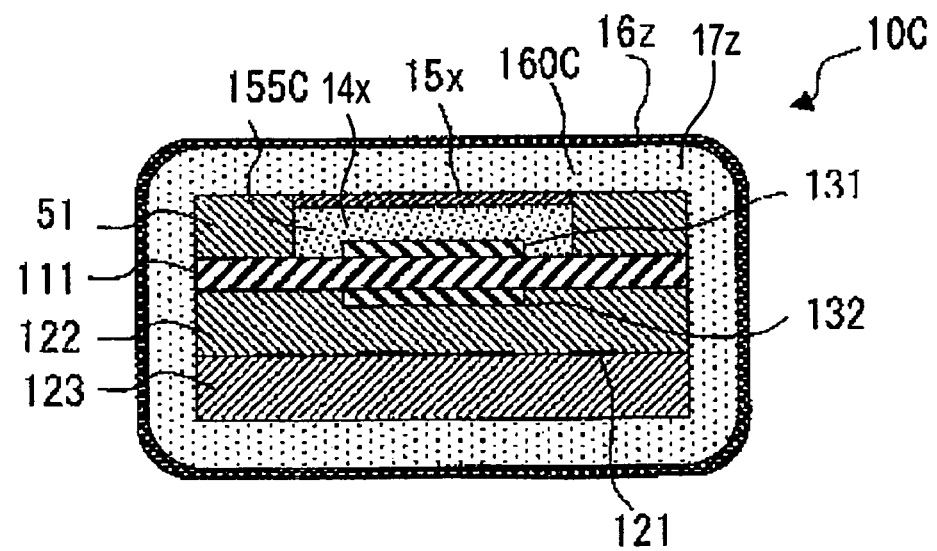
FIG. 6 is a sectional view of a gas sensor element (e.g., an oxygen sensor) according to a third embodiment of the present invention.

FIG. 6 shows a sectional view (taken in the same direction as that of FIG. 3) of a gas sensor element 10C of a gas sensor (e.g., an oxygen sensor) according to a third embodiment of the present invention. The gas sensor according to the third embodiment is the same as the gas sensor according to the first embodiment except that the porous protecting layer 155 of the first embodiment is formed as a non-particle dispersed layer, whereas the porous protecting layer of the third embodiment is formed as a particle dispersed layer. An explanation of the same portions between the first and third embodiments will be omitted.

In the gas sensor according to the third embodiment, a particle dispersed layer 160C includes an internal region 17z and a surface region 16z, and a porous protecting layer 155C includes an internal region 14x and a surface region 15x. The noble metal particles are dispersed and arranged not only in the surface region 16z of the particle dispersed layer 160C but also in the surface region 15x of the porous protecting layer 155C. Materials forming the particle dispersed layer 160C and the porous protecting layer 155C are respectively the same as those of the particle dispersed layer 160 and the porous protecting layer 155 of the first embodiment.

Kinds of elements of the noble metal particles arranged in the surface regions 16z and 15x are the same as those of the first embodiment.

The present invention is not limited to the above-described embodiments. The present invention can be applied to all gas sensors having electrodes exposed to gas to be measured. For example, the present invention may be applied to an oxygen sensor such as a full-range air-fuel ratio sensor. Although the present invention is not limited to such a use.

For example, as the oxygen sensor, an oxygen sensor including a sensor element including one electrode exposed to the outside and the other electrode facing an atmospheric air introducing chamber provided inside the sensor element.

Figure 7:
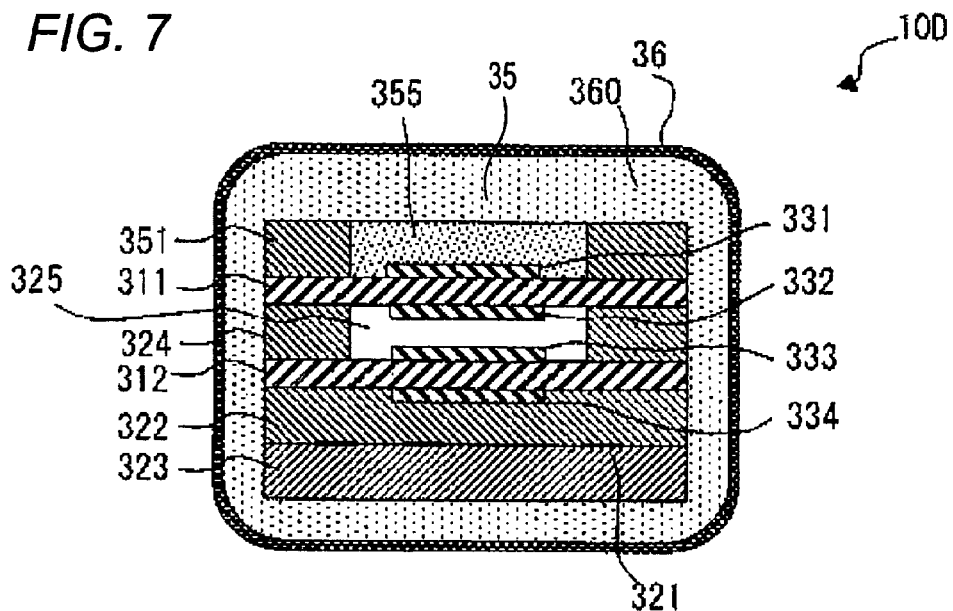
FIG. 7 is a sectional view of a gas sensor element (e.g., an oxygen sensor) according to a fourth embodiment of the present invention.

A fourth embodiment in which the present invention is applied to the full-range air-fuel ratio sensor will be described below by referring to FIG. 7. FIG. 7 shows a sectional view of the same direction as that of FIG. 3.

In FIG. 7, a gas sensor element 10D of the full-range air-fuel ratio sensor includes an oxygen pump cell and an oxygen concentration cell respectively facing upper and lower portions of a gas detecting chamber 325 to which exhaust gas is supplied. The oxygen pump cell includes: a solid electrolyte layer 311; a gas detecting chamber side electrode 332 formed on the surface of the solid electrolyte layer 311; and an electrode 331 paired with the gas detecting chamber side electrode 332. The oxygen pump cell is configured to pump oxygen in and out from the gas detecting chamber 325. The oxygen concentration cell includes a solid electrolyte layer 312; a gas detecting chamber side detecting electrode 333 formed on the solid electrolyte layer 312; and a reference electrode 334 paired with the detecting electrode and serving as an oxygen reference. The oxygen concentration cell operates as an ordinary oxygen sensor in which an electromotive force of the cell suddenly changes in the vicinity of $\lambda=1$. The gas sensor element 10D further includes a diffusion rate controlling layer 324 provided between the oxygen pump cell and the oxygen concentration cell so as to define the gas detecting chamber 325. The diffusion rate controlling layer 324 is configured to adjust an inflow rate of the gas to be measured introduced to the gas detecting chamber 325.

The gas sensor element 10D further includes two insulating layers 322 and 323 are adjacently laminated on a lower surface of the solid electrolyte layer 312, i.e., on the reference electrode 334 side of the oxygen concentration cell. A heater including heater element 321 extending in the longitudinal direction is provided between the insulating layers 322 and 323. Further, a protecting layer 355 covering the opposed electrode 331 and an insulating layer 351 enclosing the protecting layer 355 are laminated on the upper surface of the solid electrolyte layer 311, i.e., on the electrode 331 side of the oxygen pump cell. A particle dispersed layer 360 is formed to cover the oxygen pump cell, the oxygen concentration cell and the heater (their surfaces and the entire surface of laminated surfaces). The particle dispersed layer 360 serves as a water-proof layer and has an internal region 35 and a surface region 36 including noble metal particles dispersed and arranged therein as in the first embodiment.

The present invention is not limited to the above-described embodiments, and various changes and modifications can be made without departing from the technical scope of the present invention.

EXAMPLES (1) Evaluation of Dynamic Characteristics (Responsiveness) of Sensor

Example 1

A gas sensor element 10 according to the first embodiment was formed. A particle dispersed layer 160 was formed by spray injecting MgO—Al$_2$O$_3$ spinel to an end portion (a detecting portion 11) of the gas sensor element 10 so as to have a thickness of 400 μm and carrying out a thermal treatment. Thereafter, a sputtering process was carried out to a surface region 16 of the particle dispersed layer 160 by using Pt as a target and nitrogen gas for a predetermined time periods shown in FIG. 8 as described below so as to disperse Pt particles. After the sputtering process, the gas sensor element 10 was sintered in an atmospheric air at 700 to 800° C. for 10 to 60 minutes, and then, members such as a metal shell 2 was assembled to produce a gas sensor 1.

Figure 8:
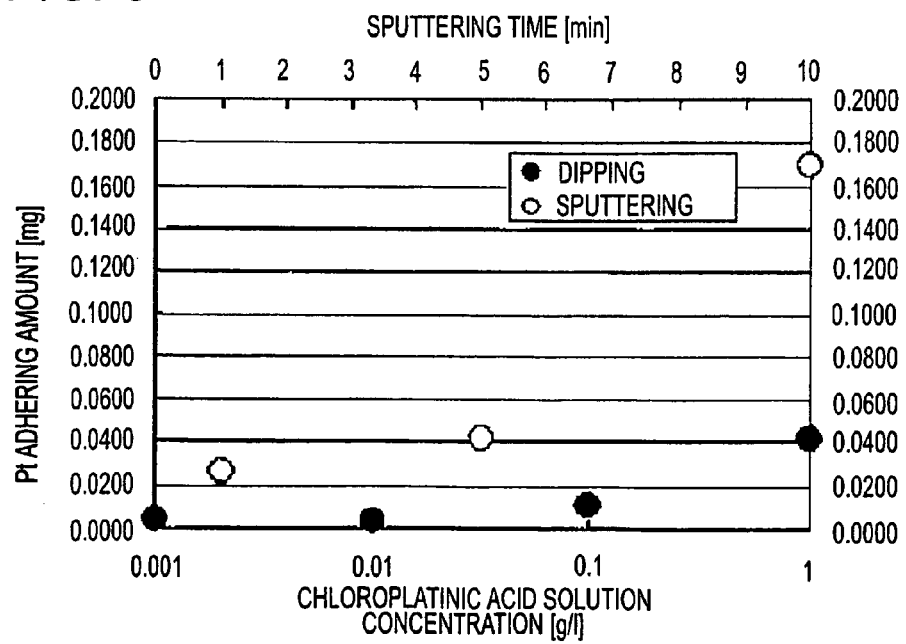
FIG. 8 is a graph showing a relationship of an amount of Pt supported by particle dispersed layer (an amount of adhesion) relative to a sputtering time and a chloroplatinic acid solution concentration.

In FIG. 8, a white circle "○" designates a relationship between a sputtering time period and an amount of adhesion of platinum (Pt). For example, when the sputtering time period was one minute, the amount of adhesion of Pt arranged per one gas sensor element 10 was about 0.025 mg. When the sputtering time period was 5 minutes, the amount of adhesion of Pt was about 0.04 mg. When the sputtering time period was 10 minutes, the amount of adhesion of Pt was about 0.17 mg.

When a section of the particle dispersed layer 160 of the Example 1 was observed by an SEM, Pt was dispersed and arranged in the surface region 16.

Comparative Example 1

A porous layer formed on the surface of the gas sensor element 10 according to the first embodiment was dipped in chloroplatinic acid solution (concentrations of 0.001 g/L to 1 g/L shown in FIG. 8) under a reduced pressure (>−0.08 MPa) for one minute and then dried in a desiccator at 100° C. to 120° C. for 10 or more minutes. After the impregnation, the gas sensor element 10 was burnt in an atmospheric air at 700 to 800° C. for 10 to 60 minutes, and then, a metal shell 2 or the like was assembled to produce a gas sensor 1.

Figure 9:
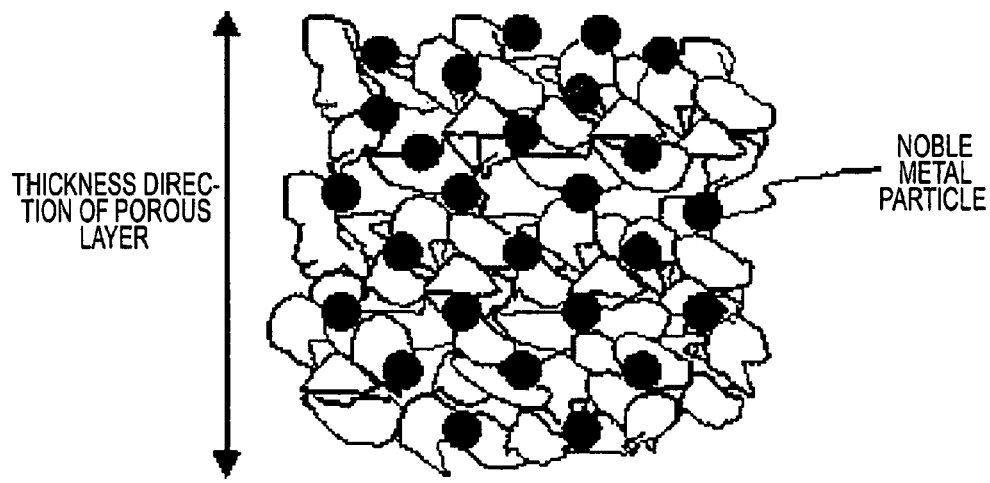
FIG. 9 is a schematic diagram showing noble metal particles adhered to an internal region of a porous layer by an impregnation method.

In FIG. 8, the black circle "●" designates a relationship between a chloroplatinic acid solution concentration and an amount of adhesion of platinum (Pt). For example, when the concentration of the chloroplatinic acid solution was 0.001 g/L, the amount of adhesion of Pt arranged per one gas sensor element was about 0.004 mg. When the concentration of the chloroplatinic acid solution was 0.01 g/L, the amount of adhesion of Pt was about 0.006 mg. When the concentration of the chloroplatinic acid solution was 0.1 g/L, the amount of adhesion of Pt was about 0.011 mg. When the concentration of the chloroplatinic acid solution was 1 g/L, the amount of adhesion of Pt was about 0.04 mg. When a section of the porous layer of the Comparative Example 1 was observed by an SEM, Pt was also supported in an internal region of the porous layer (see a schematic view of FIG. 9).

An evaluation of sensor characteristics for each of the gas sensors of the Example 1 and the Comparative Example 1 was conducted using a model gas generator using a model gas generator. The model gas of the model gas generator includes nitrogen, carbon monoxide, carbon dioxide, hydrogen, oxygen, propane, nitrogen monoxide and water vapor and forms a rich atmosphere. However, oxygen is driven at predetermined intervals to form a lean atmosphere.

Figure 10:
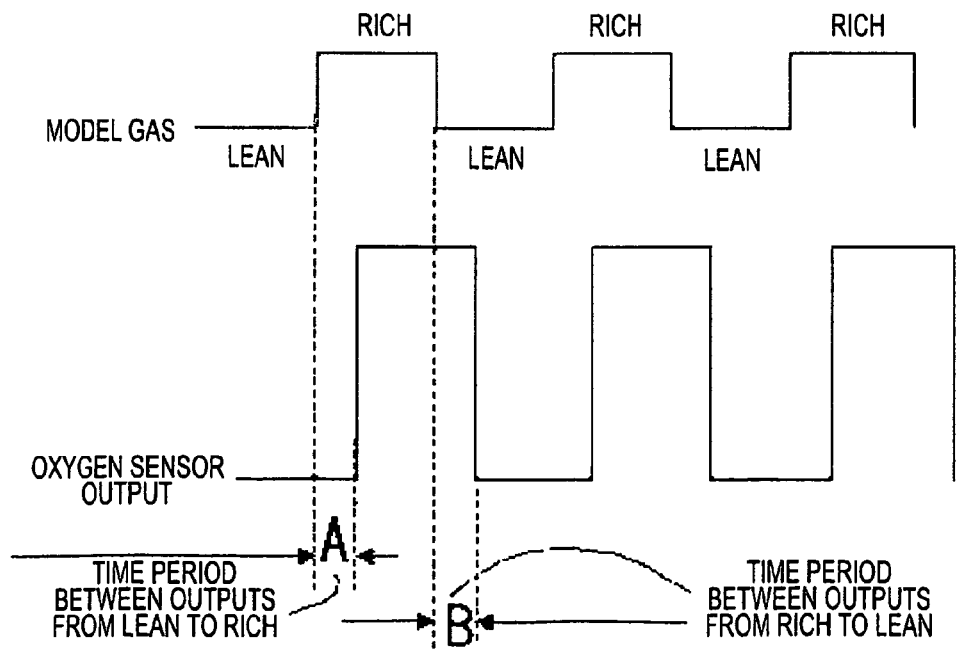
FIG. 10 is a graph illustrating dynamic characteristics (responsiveness) of an exemplary gas sensor.

Specifically, as shown in FIG. 10, a response speed was obtained as the sum of a time period A and a time period B. Herein, the time period A was defined as a time period until a rich output (an output obtained when the electromotive force suddenly changed at $\lambda=1$) was measured by the gas sensor after the model gas was switched from the lean atmosphere to the rich atmosphere. The time period B was defined as a time period until a lean output (an output obtained when the electromotive force suddenly changed in $\lambda=1$) was measured by the gas sensor after the model gas was switched from the rich atmosphere to the lean atmosphere.

Figure 11:
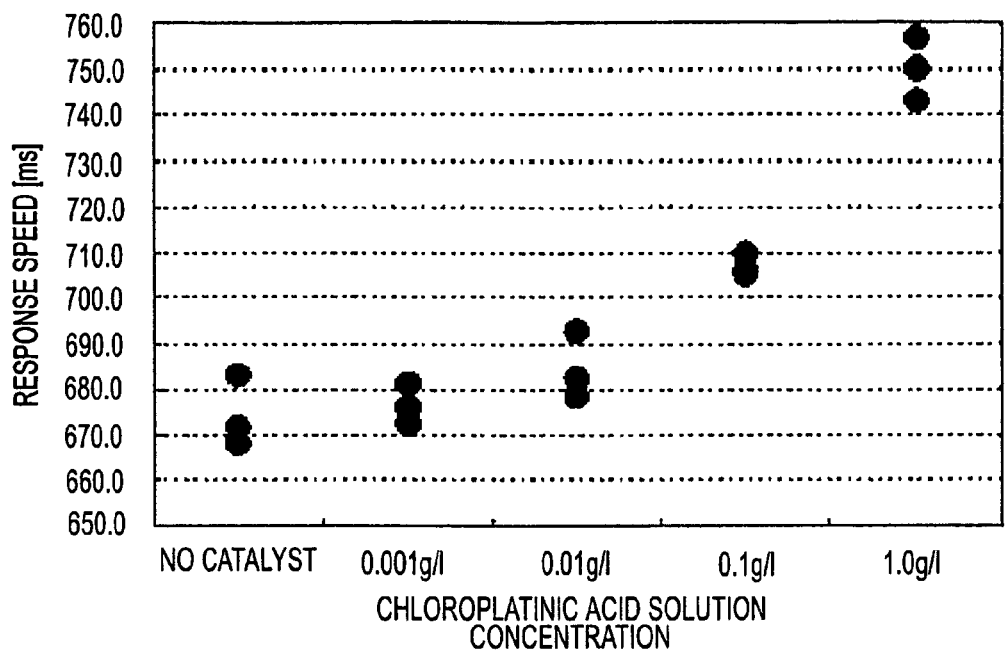
FIG. 11 is a graph illustrating response speed of an oxygen sensor of Comparative Example 1.

FIG. 11 shows the response speed obtained when the gas sensor of the Comparative Example 1 is used. As a result, when the gas sensor element was dipped in the chloroplatinic acid solution of the concentration of 0.001 g/L (an amount of adhesion of Pt was about 0.004 mg), the response speed was about 675 msec. When the gas sensor element was dipped in the chloroplatinic acid solution of the concentration of 0.01 g/L (an amount of adhesion of Pt was about 0.006 mg), the response speed was about 683 msec. When the gas sensor element was dipped in the chloroplatinic acid solution of the concentration of 0.1 g/L (an amount of adhesion of Pt was about 0.011 mg), the response speed was about 708 msec. When the gas sensor element was dipped in the chloroplatinic acid solution of the concentration of 1 g/L (an amount of adhesion of Pt was about 0.04 mg), the response speed was about 749 msec. Each response speed was an average value of data of three points.

Figure 12:
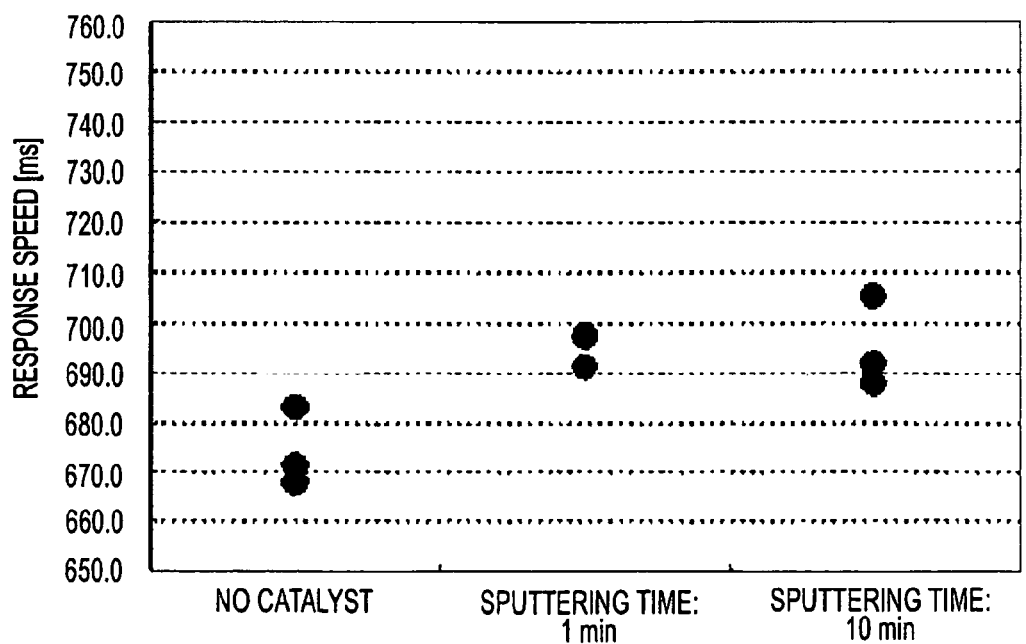
FIG. 12 is a graph illustrating a response speed of an oxygen sensor of Example 1.

On the other hand, FIG. 12 shows a response speed obtained when the oxygen sensor of the Example 1 is used. As a result, for example, when Pt particles were sputtered for one minute (an amount of adhesion of Pt was about 0.025 mg), the response speed was about 695 msec. When Pt particles were sputtered for 10 minutes (an amount of adhesion of Pt was about 0.17 mg), the response speed was about 694 msec. Then, the response speed for a gas sensor element containing Pt particles sputtered for 5 minutes (an amount of Pt particles supported by the particle dispersed layer was about 0.04 mg) was calculated using an interpolation method. According to this calculation, the response speed was 695 msec. Each response speed was an average value of data of three points.

That is, when Pt was supported by the porous layer as in the Comparative Example 1, at the time of the amount of adhesion of Pt of about 0.04 mg (the concentration of the chloroplatinic acid solution was 1 g/L), the response speed was about 749 msec. As compared therewith, when the Pt particles were arranged only in the surface region 16 of the particle dispersed layer 160 as in the Example 1, the response speed was 695 msec at the time of the amount of adhesion of Pt of about 0.04 mg (the sputtering time was 5 minutes). Thus, the deterioration of the responsiveness is suppressed.

(2) Evaluation of Static Characteristics (Relationship Between an Air Excess Ratio and Output of Sensor)

Example 2

A gas sensor element 10B according to the second embodiment was formed. A particle dispersed layer 160B was formed in such a way as described below. Initially, MgO—Al$_2$O$_3$ spinel was sprayed and injected to an end portion of the gas sensor element 10B so as to form a first particle dispersed layer 1660 having a thickness of 200 μm and then a thermal treatment was carried out. After that, a sputtering process was carried out to a surface region 16x of the first particle dispersed layer 1660 by using Pt as a target and nitrogen gas to arrange and disperse Pt particles. Then, a second particle dispersed layer 1661 having the same thickness and the same material as those of the first particle dispersed layer 1660 was formed on the surface region 16x by a spray injection and then a thermal treatment was carried out. Thereafter, Pt particles are arranged dispersed in a surface region 16y of the second particle disperser layer 1661 by a sputtering process.

After the sputtering process, the gas sensor element 10B was sintered in an atmospheric air at 700 to 800° C. for 10 to 60 minutes, and then, members such as a metal shell was assembled to produce a gas sensor 1.

In the Example 2, a sputtering time period of sputtering the Pt particles on each of the surface regions 16x and 16y was set to 2.5 minutes, and an amount of adhesion of Pt for each of the surface regions 16x and 16y was set to about 0.02 mg. Accordingly, a total amount of adhesion of Pt of the particle dispersed layer 160B was set to be the same as that of the oxygen sensor of Example 1 in which the amount of adhesion of Pt was about 0.04 mg (the sputtering time period was 5 minutes).

The oxygen sensor 1 was connected to a model gas generator to evaluate the characteristics of the sensor. The model gas of the model gas generator includes nitrogen, carbon monoxide, carbon dioxide, hydrogen, oxygen, propane, nitrogen monoxide and water vapor. The amount of oxygen and nitrogen was changed to change an air excess ratio (λ) and measure an output of the sensor in each air excess ratio λ, and measured results were plotted in FIG. 13.

The measurement was carried out by measuring the output of the sensor for 50 seconds after the elapse of 2 minutes from introducing gas having different air excess ratio λ.

Figure 13:
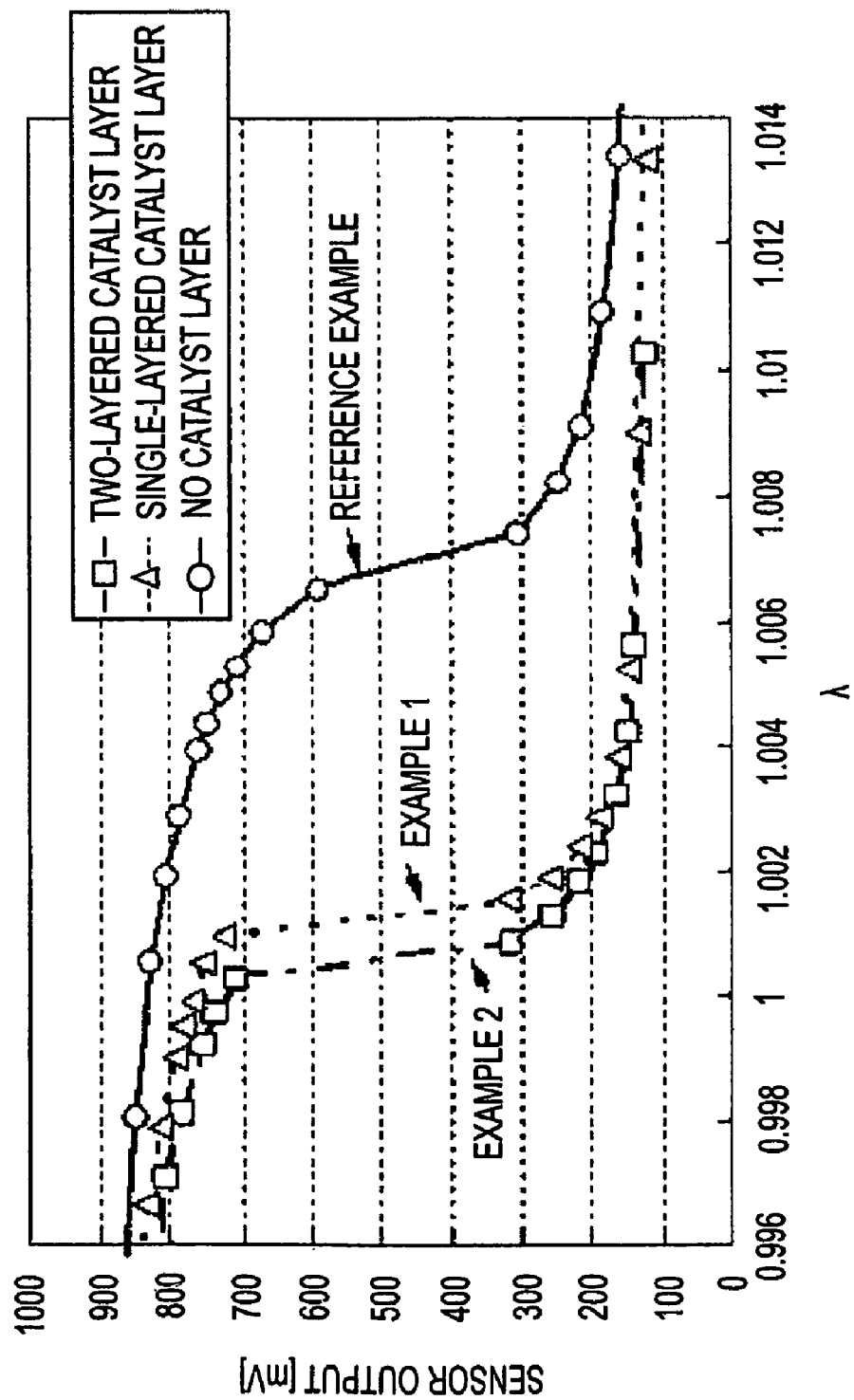
FIG. 13 is a graph illustrating measured results of the outputs of an exemplary gas sensor relative to various λ.

As shown in FIG. 13, when the oxygen sensors of the Examples 1 and 2 were used, a position where the output suddenly changes was closer to the theoretical air fuel ratio (λ=1) and a catalytic performance was higher than a Reference Example. Here, the Reference Example is prepared to include the porous layer similar to the Example 1 but not to contain the Pt particles in the porous layer. This phenomenon is considered to occur because, as the suddenly changing position of the output is closer to λ=1, reducible gas in the model gas (unburnt gas) is more burnt before the reducible gas of the model gas reaches a detecting electrode, thereby reducing an influence on the measurement. Further, in the gas sensor 1 of the Example 2, the position where the output suddenly changed was further closer to the theoretical air fuel ratio (λ=1) than that of the Example 1, and the catalytic performance was further higher than that of the Example 1.

Although the invention has been described above in relation to exemplary embodiments thereof, it will be understood by those skilled in the art that variations and modifications can be effected in these exemplary embodiments without departing from the scope and spirit of the invention.

What is claimed is:

1. A gas sensor element for detecting a specific gas component contained in a gas to be measured, said gas sensor element comprising:
    a solid electrolyte layer;
    a first electrode disposed on the solid electrolyte layer;
    a second electrode disposed on the solid electrolyte layer and paired with the first electrode; and
    a particle dispersed layer disposed on one of the first electrode and the second electrode such that the gas to be measured is introduced from outside of the gas sensor element and passes through the particle dispersed layer to at least one of the first electrode and the second electrode,
    wherein the particle dispersed layer comprises: a first porous layer comprising a first ceramic porous body which does not include noble metal particles dispersed therein; and a second porous layer provided on the first porous layer and comprising a second ceramic porous body and noble metal particles dispersed therein,
    and wherein the second porous layer defines a surface region between an outermost protruding point and a an outermost recessed point of the particle dispersed layer in the thickness direction.

2. The gas sensor element according to claim 1, wherein the noble metal particles include one or more elements selected from a group consisting of Pt, Pd, Rh and Ru.

3. The gas sensor element according to claim 1, wherein the noble metal particles are dispersed and arranged only in the second porous layer by one of a sputtering method, a PVD method and a printing method.

4. A gas sensor comprising:
    the gas sensor element according to claim 1, the gas sensor element having a plate-like shape, comprising a leading end side portion and a base end, and defining an axial direction, the leading end side portion of the gas sensor element being exposed to a gas to be measured; and a metal shell supporting the gas sensor element such that the leading end side portion protrudes from the metal shell.

5. The gas sensor element according to claim 1, further comprising:
a porous protecting layer disposed between the particle dispersed layer and one of the first electrode and the second electrode.

6. The gas sensor element according to claim 1, further comprising:
a second particle dispersed layer disposed on the particle dispersed layer such that the gas to be measured is introduced from outside of the gas sensor element and passes through the second particle dispersed layer to at least one of the first electrode and the second electrode,
wherein the second particle dispersed layer comprises: a third porous layer provided on the second porous layer, the third porous layer comprising a third ceramic porous body which does not include noble metal particles dispersed therein; and a fourth porous layer provided on the third porous layer and comprising a fourth ceramic porous body and noble metal particles dispersed therein,
and wherein the fourth porous layer defines a second surface region between an outermost protruding point and an outermost recessed point of the second particle dispersed layer in the thickness direction.

7. The gas sensor element according to claim 6, wherein an amount of the noble metal particles in the fourth porous layer is larger than an amount of the noble metal particles in the second porous layer.

* * * * *

UNITED STATES PATENT AND TRADEMARK OFFICE
CERTIFICATE OF CORRECTION

PATENT NO. : 8,088,264 B2
APPLICATION NO. : 12/349764
DATED : January 3, 2012
INVENTOR(S) : Mori et al.

It is certified that error appears in the above-identified patent and that said Letters Patent is hereby corrected as shown below:

IN THE CLAIMS:

In claim 1, col. 14, line 52, delete the word "a" to change the text to read: "region between an outermost protruding point and an"

Signed and Sealed this
Twenty-eighth Day of February, 2012

David J. Kappos
*Director of the United States Patent and Trademark Office*